United States Patent
Rao (10) Patent No.: US 7,556,598 B2
(45) Date of Patent: Jul. 7, 2009

(54) DISSOLVABLE PROTECTIVE TREATMENT FOR AN IMPLANTABLE SUPPORTIVE SLING

(75) Inventor: Doreen Rao, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 620 days.

(21) Appl. No.: 11/098,178

(22) Filed: Apr. 4, 2005

(65) Prior Publication Data
US 2006/0224038 A1 Oct. 5, 2006

(51) Int. Cl.
*A61F 2/02* (2006.01)
(52) U.S. Cl. ..................................................... 600/30
(58) Field of Classification Search ............... 600/29, 600/30, 37, 31–32; 606/151, 185, 154; 128/898, 128/DIG. 25
See application file for complete search history.

(56) References Cited

U.S. PATENT DOCUMENTS

| 6,042,534 | A | 3/2000 | Gellman et al. |
| 6,042,592 | A | 3/2000 | Schmitt |
| 2004/0015044 | A1 | 1/2004 | Zappala |
| 2004/0143152 | A1* | 7/2004 | Grocela ..................... 600/30 |
| 2005/0027220 | A1* | 2/2005 | Wagner et al. ............... 602/4 |
| 2006/0183966 | A1* | 8/2006 | Neisz et al. ................. 600/30 |
| 2006/0205998 | A1* | 9/2006 | Li et al. ..................... 600/30 |

FOREIGN PATENT DOCUMENTS

| EP | 0677297 B1 | 10/1995 |
| EP | 1151722 B1 | 11/2001 |
| WO | WO98/35632 | 8/1998 |
| WO | WO02/19945 | 3/2002 |
| WO | WO03/007847 | 1/2003 |
| WO | WO03/105727 | 12/2003 |
| WO | WO2004/043294 | 5/2004 |
| WO | WO2005/011771 | 2/2005 |

OTHER PUBLICATIONS

Amid, et al., "Experimental Evaluation of a New Composite Mesh with the Selective Property of Incorporation to the Abdominal Wall Without Adhering to the Intestines," *Journal of Biomedical Materials Research*, 28:373-375 (1994).
Carachi, et al., "Collagen-Coated Vicryl Mesh: A New Bioprosthesis in Pediatric Surgical Practice," *Journal of Pediatric Surgery*, 30(9):1302-1305 (1995).
Hakim, et al., "Use of Biodegradable Mesh as a Transport for a Cultured Uroepithelial Graft: An Improved Method Using Collagen Gel," *Urology*. Jul. 1994, 44(1):139-42.
Matapurkar, *World J Surg*. Sep.-Oct. 1993 17(5):683.
Olsen, et al., "Urethral Reconstruction with a New Synthetic Absorbable Device," *Scand J Urol Nephrol*., 26(4):323-6 (1992).
Ulmsten, et al., "An Ambulatory Surgical Procedure Under Local Anesthesia for Treatment of Female Urinary Incontinence," *Int. Urogynecol J*, 7:81-86 (1996).
Carachi, R. et al. Collagen-Coated Vicryl Mesh: A New Bioprostheis in Pediatric Surgical Practice.

* cited by examiner

*Primary Examiner*—John P Lacyk
(74) *Attorney, Agent, or Firm*—Ropes & Gray LLP (57) ABSTRACT

The invention provides, in one embodiment, a sling assembly including an implantable supportive sling and a biocompatible dissolvable protective treatment on at least a portion of the sling.

25 Claims, 4 Drawing Sheets

DISSOLVABLE PROTECTIVE TREATMENT FOR AN IMPLANTABLE SUPPORTIVE SLING

TECHNICAL FIELD

The invention generally relates to surgical sling assemblies, and related methods, for providing anatomical support in a patient's body. More particularly, in various embodiments, the invention relates to dissolvable coatings for implantable supportive slings.

BACKGROUND INFORMATION

Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI involves implanting a supportive sling under a patient's bladder neck or mid-urethra to provide a urethral platform. Placement of the surgical sling limits the endopelvic fascia drop while providing compression to the urethral sphincter to improve coaptation. Typically, a protective sleeve encloses the sling during the placement procedure. Once the surgical sling assembly, which includes the sling and the sleeve, is correctly positioned in the patient's periurethral tissues, the sleeve is physically removed from about or slid off the sling and withdrawn from the patient's body, leaving behind only the sling in the patient's tissues.

However, the current steps and procedures used to physically remove the sleeve from about the sling that it encloses are problematic. For example, while physically removing the sleeve from about the sling, friction between the sleeve and the sling may cause the sling to be dragged away from its preferred position adjacent the mid-urethra, to twist, or to otherwise become misplaced. Ultimately, the utility of the sling is hampered and patient discomfort is increased.

Accordingly, improved surgical sling assemblies and related methods for treating SUI are needed.

SUMMARY OF THE INVENTION

The invention addresses the deficiencies in the prior art by, in one embodiment, providing an implantable surgical sling assembly having a dissolvable biocompatible protective treatment, and related methods, for providing anatomical support in the periurethral tissue of a patient's body (e.g., for providing a urethral platform). The surgical sling assembly and related methods of the invention have the advantage over the prior art of obviating the need for physically removing a protective sleeve from about a sling, while still providing sufficient structural protection and rigidity to inhibit sling deformation during implantation. As used herein, the term "biocompatible" refers to a material that is substantially non-toxic and that does not induce a significantly adverse effect on the patient's health.

According to one aspect, the invention provides a sling assembly for treating urinary incontinence. The sling assembly includes an implantable supportive sling having first and second sides and first and second longitudinally extending edges and is sized and shaped for being placed in the periurethral tissue to provide a urethral platform. The first and second longitudinally extending edges may include, for example, tanged or relatively smooth untanged sections. The sling may be made for example from any suitable synthetic and/or natural material, and may be formed as a mesh or other suitable structure, such as a sheet of material. The sling assembly includes a biocompatible dissolvable protective treatment that covers at least a portion of the first longitudinally extending edge of the sling along at least the first side of the sling. The protective treatment leaves a longitudinally extending portion of the sling intermediate to the first and second edges untreated along at least a portion of its length.

According to one configuration, an intermediate strip along substantially the entire length of the sling is left untreated. The biocompatible dissolvable treatment dissolves into the bodily fluids or leaches into the patient's tissues in the region of the sling subsequent to implantation. According to one feature, the biocompatible dissolvable protective treatment provides sufficient structural rigidity to inhibit the sling from stretching or otherwise deforming longitudinally during implantation. According to another feature, the protective treatment inhibits the sling from twisting axially and/or deforming horizontally during implantation.

According to some embodiments, the protective treatment covers at least a portion of the first longitudinally extending edge of the sling along both the first and second sides of the sling. According to a further embodiment, the protective treatment also covers at least a portion of the second longitudinally extending edge along at least one of the first and second sides. In one configuration, the protective treatment covers the first longitudinally extending edge of the sling along the first side along substantially the entire length of the sling.

The protective treatment may be applied to the sling, for example, by way of spraying, brushing or dipping the portion of the sling to be treated. In an alternative embodiment, the protective treatment is in the form of a sheet of material affixed to the portion of the sling to be treated. According to another embodiment, the protective treatment is applied as one or more flattened tubes slid over the sling. In a further embodiment, the protective treatment includes a polymer, which is melted, freeze dried, or vacuum dried on to the sling. In one implementation, the protective treatment ultimately assumes the characteristics of a gel or solidifies. Additionally, more than one protective or other treatment, of the same or different materials, may be applied, in the same or different manners, to the sling.

In one configuration, the protective treatment substantially encapsulates a portion of the first longitudinally extending edge along both the first and second sides of the sling. In another configuration, the protective treatment also substantially encapsulates a portion of the second longitudinally extending edge along both the first and second sides of the sling. According to one feature of this configuration, the protective treatment is of sufficient rigidity to prevent any tanged or ragged sections of the longitudinally extending edges from catching on the patient's tissues during the delivery procedure.

According to a further embodiment, the sling includes first and second terminal ends and an intermediate portion located intermediate to the first and second terminal ends and extending across the width of the sling. Preferably, the intermediate portion is located near a middle location along the length of the sling and extends across the width of the sling between the first and second longitudinally extending edges. According to one feature, the intermediate portion is devoid of the biocompatible bioabsorbable treatment on at least a urethra facing side of the sling, to reduce the likelihood of irritating the tissue immediately surrounding the urethra. In one configuration, the first side of the sling is the urethra facing side. In other configurations, the second side of the sling is the urethra facing side.

The treatment may include a plurality of compounds. By way of example, the treatment may include any or a combination of an alginate, a sugar based formulation, a starch, a gelatin, cellulose, polyvinyl alcohol, polyglycolic acid, polylactic acid, polydioxinone, and/or a lubricious material. According to another feature, the treatment may be configured to dissolve within a particular time range. For example, the treatment may be configured to be substantially dissolved within about 30, 15, 10 or 5 minutes from the time the sling is implanted.

Thus, according to various embodiments, the invention improves over the prior art by providing a biocompatible absorbable protective treatment for implantable slings, wherein the treatment, does not necessarily cover, coat, encapsulate or otherwise treat the entire sling. The protective treatment of the invention may also include any suitable therapeutic agent for absorption into the patient's tissues.

The foregoing and other objects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION OF ILLUSTRATIVE EMBODIMENTS

As described above in summary, the invention provides in various illustrative embodiments an implantable surgical sling having a dissolvable biocompatible protective treatment, and related methods, for providing anatomical support in the periurethral tissue of a patient's body (e.g., for providing a urethral platform).

Figure 1A:
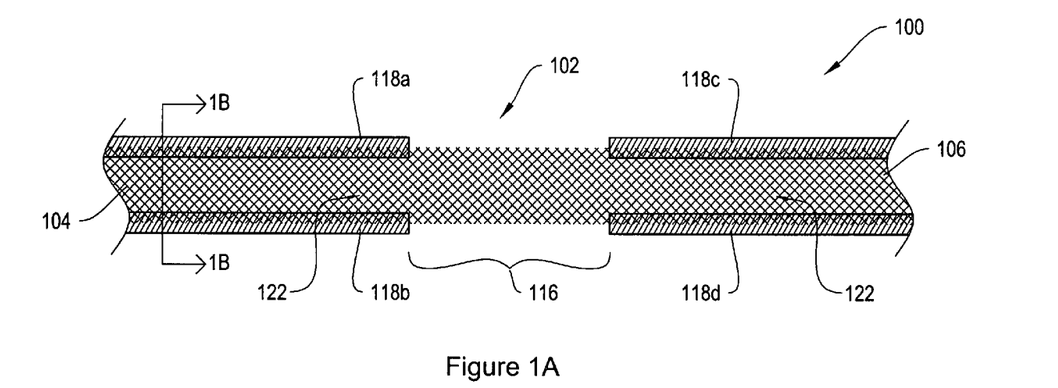
FIG. 1A is a top view of a sling assembly including a dissolvable biocompatible protective treatment according to an illustrative embodiment of the invention.
Figure 1B:
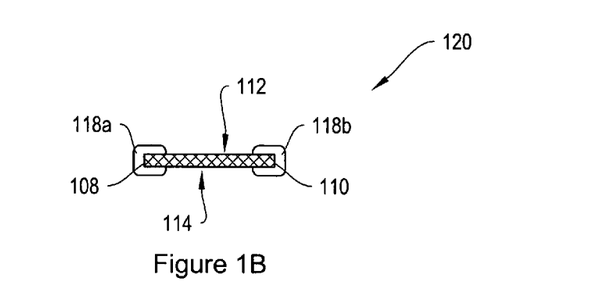
FIG. 1B is a cross-sectional end view of the sling assembly of FIG. 1A.

FIG. 1A shows a top view of a sling assembly 100 including a sling 102 having dissolvable biocompatible protective treatment 118 according to an illustrative embodiment of the invention. FIG. 1B shows a cross-sectional end view 120 of the sling assembly 100 taken along line AA. Referring to both FIGS. 1A and 1B, the sling 102 has first 104 and second 106 terminal ends. It also has first 112 and second 114 sides and first 108 and second 110 longitudinally extending edges. According to the illustrative embodiment of FIGS. 1A and 1B, the edges 108 and 110 have V-shaped projections or are frayed (e.g., tanged). However, in alternative embodiments, the edges 108 and 110 may be linear in nature (e.g., relatively smooth and not tanged). The sling 102 also has an intermediate section 116 located about mid-way between the first 104 and second 106 terminal ends and extending between the first 108 and second 110 edges. As described below, the terminal ends 104 and 106 of the sling 102 may terminate in any suitable mechanism for associating the sling 102 with a suitable delivery device or for employing any suitable delivery approach.

According to various illustrative configurations, one feature of the protective treatment 118 is that it eliminates the need for employing, and then physically removing from about the sling subsequent to placement, a protective sleeve. The protective treatment 118 also provides sufficient structural protection and rigidity (similar to that of a protective sleeve) to inhibit the sling from deforming, twisting or becoming otherwise damaged during implantation. Exemplary bioabsorbable/dissolvable materials from which the protective treatment 118 may be made include, but are not limited to, alginates, sugar based formulations, starches, gelatins, cellulose, polyvinyl alcohol, polyglycolic acid (PGA), polylactic acid (PLA), polydioxinone (PDO), and/or other synthetic or natural polymers including combinations thereof.

The biocompatible protective treatment 118 may cover any portion or all of the sling 102. According to the illustrative embodiment of FIGS. 1A and 1B, the biocompatible dissolvable protective treatment 118 includes at least a section 118a that covers at least a portion of the first longitudinally extending edge 108 of the sling 102. The protective treatment 118a extends along at least the first side 112 of the sling 102. However, as shown in FIG. 1B, the protective treatment 118a may also extend along the second side 114 of the sling. In the illustrative sling assembly 100, the protective treatment 118 leaves a longitudinally extending portion 122 of the sling 102 intermediate to the first and second edges 108 and 110 untreated along at least a portion of its length. Although FIG. 1A depicts the intermediate portion 122 as being untreated along its entire length, this need not be the case. The protective treatment 118 of the sling assembly 100 also includes a section 118b that extends along at least a portion of the second longitudinally extending edge 110 of the sling 102. As in the case of the section 118a, the section 118b may extend along one or both of the first 112 and second sides 114 of the sling 102.

In one particular configuration, the protective treatment 118a encapsulates or substantially encapsulates at least portion of the first longitudinally extending edge 108 along both the first 112 and second 114 sides of the sling 102. In a related configuration, the protective treatment 118b also encapsulates or substantially encapsulates at least a portion of the second longitudinally extending edge 110 along both the first 112 and second 114 sides of the sling 102. According to one feature, the protective treatment 118 is formed from lubricious material and reduces the friction between the sling assembly 100 and the patient's periurethral tissues. In this way, the protective treatment 118 of the invention can provide a relatively smooth tissue contact surface to otherwise tanged or ragged sling edges 108 and 110 to reduce the likelihood of the sling 102 irritating the patient's tissues during implantation.

Although the protective treatment 118a and 118b may extend along the entire or substantially the entire length of the sling 104, as shown in FIG. 1A, in other illustrative embodiments, the intermediate portion 116 is left untreated on one or both of sides 112 and 114. In one particular configuration, the side of the sling 102 that faces the urethra when implanted is left devoid of the treatment 118. In various illustrative embodiments, the mid-length section has a length of about 1 cm to about 2 cm, about 500 mm to about 1 cm, or about 250 mm to about 500 mm.

The protective treatment 118 may be applied to the sling 108 by any suitable approach, for example, by way of spraying, brushing or dipping the portion of the sling to be treated. According to another illustrative embodiment, the protective treatment 118 is formed as a sheet of material that can be affixed to the portion of the sling 102 to be treated.

According to another feature, the treatment may be configured to dissolve within a particular time range. The treatment may be configured, for example, to substantially absorb into the patient's tissues within about 30, 15, 10 or 5 minutes from the time the sling is implanted.

Although the protective treatment 118 is depicted in FIGS. 1A and 1B as being employed with a particular mesh sling 102, it may be employed with any suitable implantable sling. The protective treatment 118 may be employed with a sling 102, for example, being in the range of about 5 cm to about 50 cm in length, and about 0.5 cm to about 3 cm wide, though larger or smaller slings may be employed to suit the size of the patient and/or the application. The thickness of the sling 102 may be uniform over the entire sling, or the thickness may vary at one or more different locations. According to various illustrative embodiments, the thickness of the sling 102 ranges from about 0.01 cm to about 0.2 cm, and in one embodiment is about 0.08 cm.

The treatment 118 may be employed with a sling 102 having any suitable shape and including any complimentary features. By way of example, the sling 102 may be rectangular or substantially rectangular, trapezoidal, hexagonal, octagonal or elliptical in shape, as may be suitable for its intended location at a particular anatomical site. The sling 102 may also have a forked configuration at one or both ends. As mentioned above, in some illustrative embodiments, the edges of the sling may be linear in nature (e.g., relatively smooth and not tanged) or may have V-shaped projections or be frayed (e.g., tanged) at the edge. In some illustrative embodiments, the sling 102 includes apertures, of any suitable shape and size, for example, round, square, diamond-shaped, or triangular. In other illustrative embodiments, at least one of the sides of the sling 102 is textured. The textured or irregular surface acts to enhance tissue growth into the sling and also aids in stabilization of the sling in the tissue through frictional forces. Without limitation, examples of various sling configurations that may be with illustrative embodiments of the invention are disclosed in U.S. Ser. No. 10/092,872, entitled "Medical slings," U.S. Ser. No. 10/640,838, entitled "Medical implant," U.S. Ser. No. 10/641,170, entitled "Medical slings," and U.S. Ser. No. 10/641,192, entitled "Medical slings," the entire contents of all of which are incorporated by reference below.

According to another illustrative embodiment, the treatment 118 may be employed with a sling 102 that includes a tensioning mechanism for limiting its stretchability, aiding in the application of even tension along its length, and aiding in preventing it from becoming misshapen subsequent to placement. Such tensioning mechanism may be embedded in the sling material and/or may be made from resorbable or non-resorbable suture material. The tensioning device may be substantially linear or coiled. Examples of resorbable suture materials include, without limitation, polylactic acid (PLA), polyglycolic acid (PGA), and poly-L-lactic acid (PLLA). Examples of non-resorbable suture materials include, without limitation, polypropylene (PP) and polybutester. Without limitation, examples of tensioning mechanisms that may be employed with illustrative embodiments of the invention are disclosed in U.S. Pat. No. 6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," the entire contents of all of which are incorporated below by reference.

According to other illustrative embodiments, the treatment 118 of the invention may be employed with any suitable delivery system. Such delivery systems include, for example, those delivery systems configured for supra-pubic, pre-pubic, transvaginal, and/or transobtural procedures. Without limitation, examples of sling assemblies, delivery devices and implantation approaches that may employ illustrative embodiments of the invention are disclosed in U.S. Ser. No. 10/015,114, entitled "Devices for minimally invasive pelvic surgery," U.S. Ser. No. 10/774,826, entitled "Devices for minimally invasive pelvic surgery," U.S. Ser. No. 10/093,398, entitled "System for implanting an implant and method thereof," U.S. Ser. No. 10/093,498, entitled "System for implanting an implant and method thereof," U.S. Ser. No. 10/093,371, entitled "System for implanting an implant and method thereof," U.S. Ser. No. 10/093,424, entitled "System for implanting an implant and method thereof," U.S. Ser. No. 10/093,450, entitled "System for implanting an implant and method thereof," U.S. Ser. No. 10/094,352, entitled "System for implanting an implant and method thereof," U.S. Ser. No. 10/631,364, entitled "Bioabsorbable casing for surgical sling assembly," U.S. Ser. No. 10/641,376, entitled "Spacer for sling delivery system," U.S. Ser. No. 10/641,487, entitled "Systems, methods and devices relating to delivery of medical implants," U.S. Ser. No. 10/642,395, entitled "Systems, methods and devices relating to delivery of medical implants," U.S. Ser. No. 10/642,397, entitled "Systems, methods and devices relating to delivery of medical implants," U.S. Ser. No. 10/832,653, entitled "Systems and methods for sling delivery and placement," U.S. Provisional Application No. 60/569,300, entitled "Systems and methods for delivering a medical implant to an anatomical location in a patient," and U.S. Provisional Application No. 60/508,600 entitled "Systems and methods for delivering a medical implant to an anatomical location in a patient," the entire contents of all of which are incorporated below by reference.

According to another feature, at least a portion of the sling 102 is biodegradable and may also dissolve and/or be absorbed into the patient's tissues. For example, in one illustrative embodiment, the fibers of the sling 102 are biodegradable. In other illustrative embodiments, only a section of the sling 102, such as, for example, the intermediate section 102, is biodegradable. Exemplary biodegradable materials, in addition those listed above, which may be employed for the sling 102 and/or the protective treatment 118 include, but are not limited to, human dermis and decellularized animal tissue. Human tissues may be derived, for example, from human cadaveric or engineered human tissue. Animal tissues may be derived, for example, from porcine, ovine, bovine, and equine tissue sources. Additionally, exemplary biodegradable polymers, which may be employed in addition to those listed above, for the protective treatment 118 and/or a portion of the sling 102 include, but are not limited to, polylactic acid, polyglycolic acid and copolymers and mixtures thereof, such as poly(L-lactide) (PLLA), poly(D,L-lactide) (PLA), polyglycolic acid[polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof. The sling material may also be made of a combination of mammalian tissue and synthetic material(s).

According to another illustrative feature, the sling 102 and/or the protective treatment 118 may also include an agent for release into the patient's tissues. One illustrative agent promotes, when applied to the patient's tissues in a pharmaceutically acceptable amount, well-organized collagenous tissue growth, such as scar tissue growth, preferably, in large quantities. According to one feature, the agent 108 may or may not block or delay the dissolvability of the protective treatment 118. This may be controlled by selecting differing methods for loading the agent onto the sling 102 or protective treatment 118. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues. In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrphine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that maybe combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfiric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-ltrimethyl-3,3-diphenyl-propylamine, tropenzile, trospium chloride, xenytropium bromide, and pharmaceutically acceptable salts thereof.

The agent may be associated with the sling 102 and/or the protective treatment 118 in a variety of manners. For example, the agent may be chemically or physically attached to the surface of one or more of the fibers of the sling 102. In one illustrative embodiment, the surface of the sling 102 (and/or the protective treatment 118) and the agent, for example, in solution, have complementary ionic charges. As such, when placed on the sling 102 (and/or the protective treatment 118), the agent ionically bonds to its surface. In another illustrative embodiment, before application of the agent, the protective treatment 118 is applied to the sling 102. According to another illustrative embodiment, the protective treatment 118 and the agent are mixed to form a single treatment and then applied to the sling in a one step process. According to the invention, any suitable process may be employed for associating the agent and/or the treatment 118 with the sling 102, such that the agent can leach to tissue in the region of the implanted sling 102 and the treatment 118 can dissolve into the bodily fluids and/or leach into the tissue in the region of the implanted sling 102.

Figure 2A:
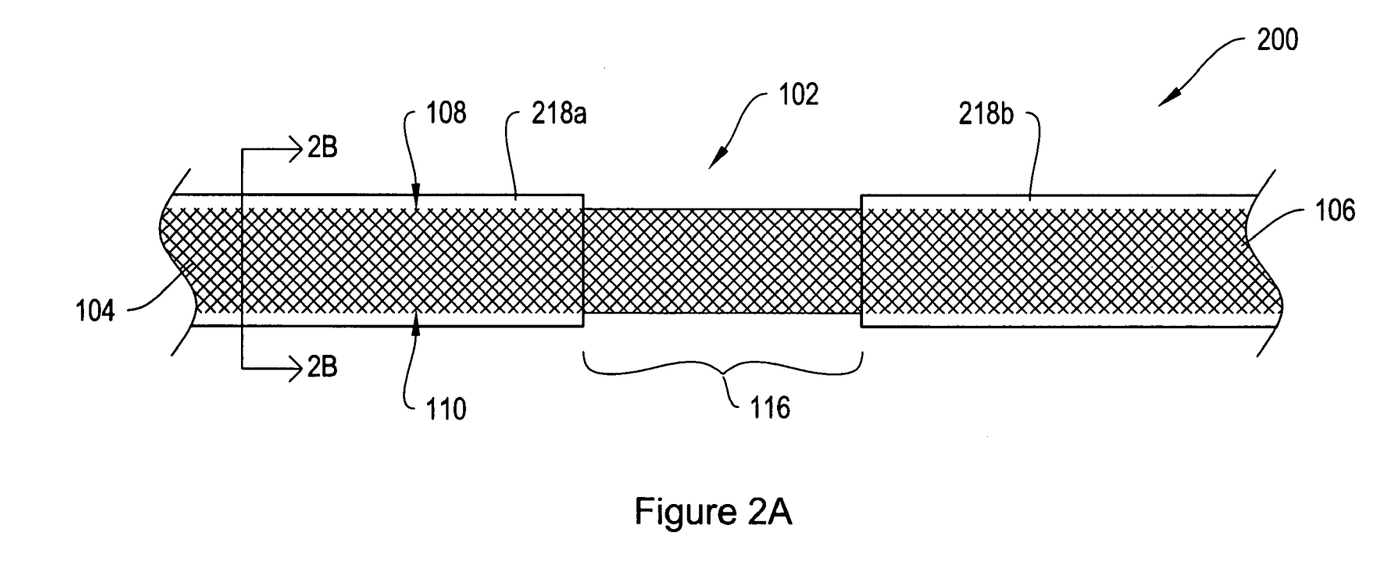
FIG. 2A is a top view of a sling assembly including a dissolvable biocompatible protective treatment according to another illustrative embodiment of the invention.
Figure 2B:
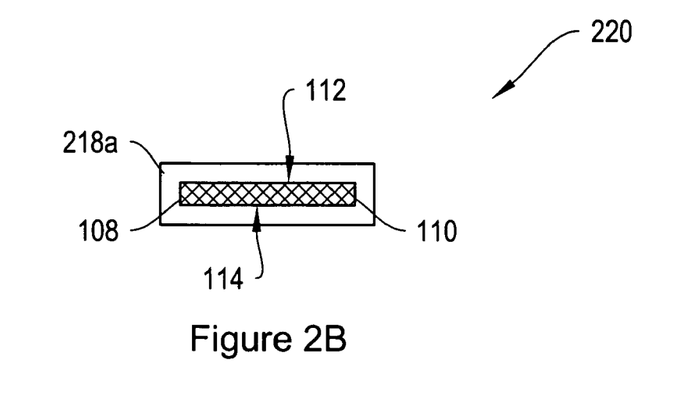
FIG. 2B is a cross-sectional end view of the sling assembly of FIG. 2A.

FIG. 2A depicts a top view of sling assembly 200 according to another illustrative embodiment of the invention. FIG. 2B is a cross-sectional end view 220 of the sling assembly 200 taken along the line BB. The sling assembly 200, like the sling assembly 100 of FIGS. 1A and 1B, includes a sling 102 having first 104 and second 106 terminal ends, first 108 and second 110 longitudinally extending edges, and an intermediate section 116. Referring to FIGS. 2A and 2B, the illustrative sling assembly 200 includes a biocompatible dissolvable protective treatment 218. The illustrative protective treatment 218 may include any or all of the features of the above described protective treatment 118. However, rather than leaving a longitudinally extending portion 122 untreated, the protective treatment 218 includes a section 218a, which substantially encapsulates a portion of the sling 102. Although the protective treatment 218a is shown as substantially encapsulating a portion of the sling 102, this need not be the case. By way of example, in alternate illustrative embodiments, the protective treatment 218a extends along only one side 112 or 114 of the sling 102.

The protective treatment 218a may extend along the entire length of the sling 102. Alternatively, the protective treatment 218 may include a section 218b axially spaced apart from the section 218a along the sling 102. As shown in FIG. 2A, one advantage of this configuration is that the intermediate portion 116 of the sling 102 may be left devoid of a protective treatment should that be desired. According to the illustrative embodiment of FIG. 2A, the intermediate portion 116 has relatively smooth un-tanged edges to further reduce the likelihood of irritating the patient's urethral. However, this need not be the case. The protective treatment 218a and 218b may be applied to the sling 102, for example, by any of the ways described above with respect to the protective treatment 118.

Additionally, in the case where the protective treatment 118 encapsulates a portion of the sling 102, it may also be applied as one or more flattened tubes slid over the sling 102.

In an exemplary method of treating urinary incontinence using the invention, a medical operator selects a sling assembly including a protective treatment having the desired dissolvability qualities along with any desired leaching agents, and places the sling assembly in the periurethral tissue of a patient adjacent to the patient's urethra by any suitable approach, such as any of those mentioned above. The protective treatment and (optionally) any agents then dissolve into the patient's body in accord with the particular qualities of the selected sling assembly, thereby obviating the need for the medical operator physically removing a protective sheath from the sling subsequent to placement.

Illustratively, the medical operator introduces a shaft having a first end of the sling assembly associated therewith into the patient's body transvaginally at a first site on a first side of the urethra, and causes the distal end of the shaft to emerge from the patient's abdominal wall. The operator then grasps and stabilizes the first end of the sling assembly and backs the shaft out of the patients body. The operator then repeats the process on the contralateral side of the patient's body for the second end of the sling assembly.

In alternative embodiments, rather than using a transvaginal approach as described above, the operator approaches the patient's periurethral tissues using a supra-pubic approach (i.e., percutaneously through the abdominal wall, abdominal fascia, and rectus fascia), a transobturator approach (i. e., around the ischiopubic ramus percutaneously through the obturator membrane and periurethral endopelvic fascia to a vaginal incision or from a vaginal incision through the periurethral endopelvic facia and obturator membrane and out around the ischiopubic ramus), or a pre-pubic approach (i. e., from the abdominal wall along the anterior surface of the pubic bone).

Figure 3A:
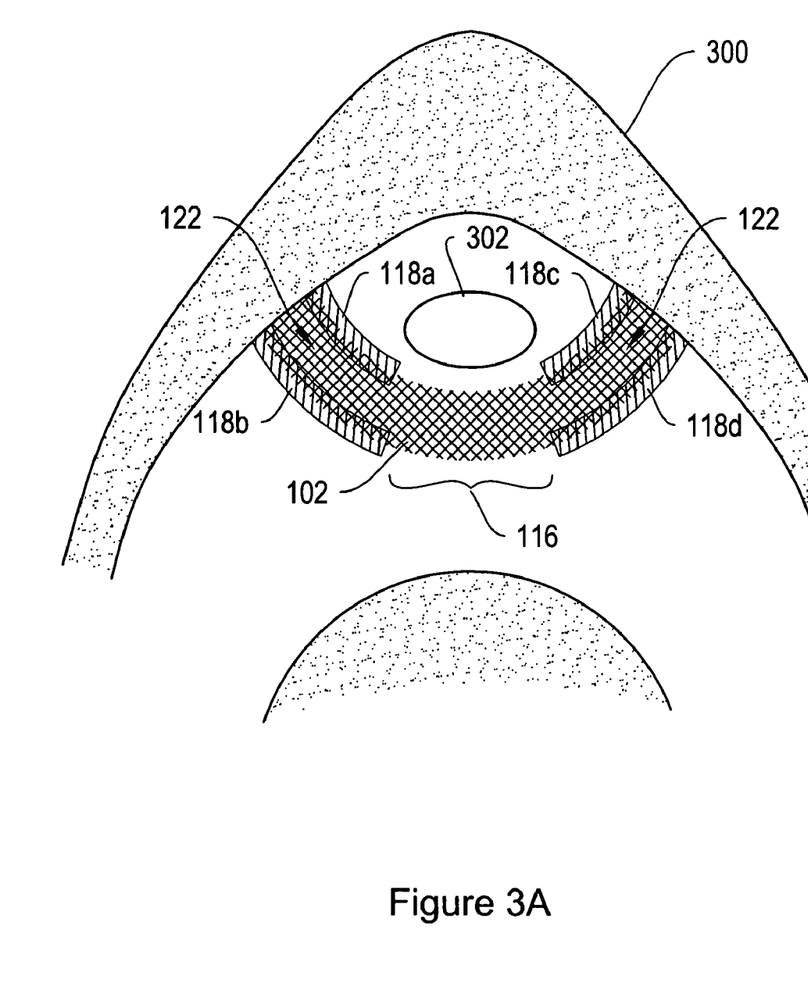
FIG. 3A is a conceptual diagram depicting a sling assembly having a biocompatible dissolvable protective treatment according to an illustrative embodiment of the invention implanted in the periurethral tissue of a patient.
Figure 3B:
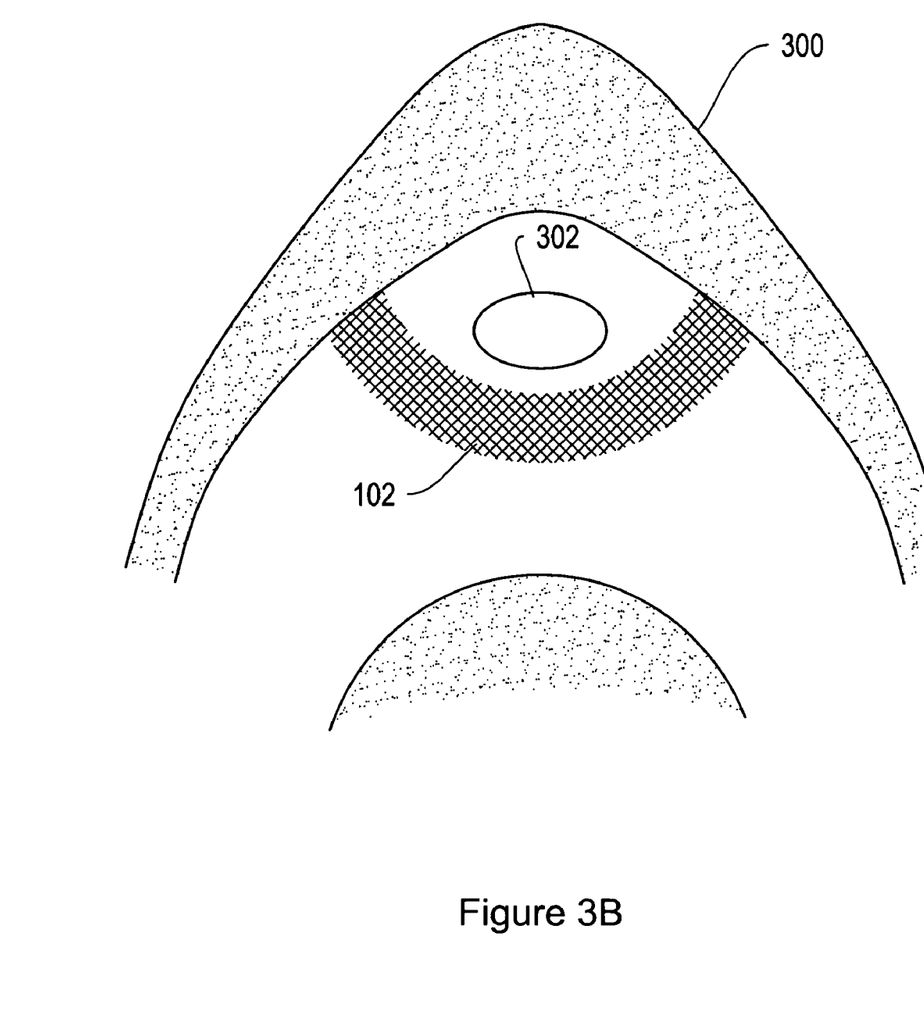
FIG. 3B is a conceptual diagram of the implanted sling assembly of FIG. 3A subsequent to the protective treatment dissolving into the body of the patient.

FIG. 3A is a conceptual diagram depicting the sling assembly 100 of FIG. 1 implanted in the periurethral tissue 300 of a patient according to one illustrative embodiment of the invention. The urethra is indicated at 302. As depicted, when initially implanted the sling assembly 100 includes the biocompatible dissolvable treatment 118a-118d. However, as shown in FIG. 3B, after a pre-determined period of time, such as, for example, less than about 30, 20 or 10 minutes after placement in the patient's periurethral tissues 300, the protective treatment 118a-118d dissolves and is absorbed by the patient's body. Preferably, the protective treatment 118a-118d is absorbed by the patient's tissues within about 5 to about 15 minutes after placement of the sling assembly 100. However, in alternate embodiments, the protective treatment 118a-118d may be absorbed by the patient's body after any period of time following placement. Ultimately, only the sling 102 is left behind in the patient's periurethral tissues 300, and in some embodiments, even the sling may dissolve after a period of time. In cases where the sling does not dissolve, tissue compression and eventual tissue in-growth along the length of the sling 102 permanently secures it in position. The sling 102, along with the scar tissue formed there around, provides the requisite support for maintaining continence.

As described above, the dissolvable biocompatible protective treatment described herein may be employed with any suitable sling or sling assembly. A sling or sling assembly employing the treatment of the invention may be delivered to an anatomical site in a patient's body by way of any suitable delivery device or delivery approach, including by way of an abdominal (e.g., supra-pubic), transvaginal, transobtural, or pre-pubic approach. Also, the sling or sling assembly may employ any suitable sling assembly-to-delivery device association mechanism. Once implanted, the sling may employ any suitable anchoring mechanism or none at all.

Without limitation, examples slings, sling assemblies, sling delivery devices and approaches, sling assembly-to-delivery device association mechanisms, and sling anchoring mechanisms with which the invention may be employed disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669, 706, entitled "Thin soft tissue surgical support mesh," U.S. Pat. No. 6,752,814, entitled "Devices for minimally invasive pelvic surgery," U.S. patent application Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642, 395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093, 450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

What is claimed is:

1. A sling assembly for treating urinary incontinence comprising, an implantable supportive sling having first and second sides and first and second longitudinally extending edges and being sized and shaped for providing a urethral platform, and a biocompatible dissolvable protective treatment along at least a portion of the first longitudinally extending edge of the sling along at least the first side of the sling, the sling having a longitudinally extending portion intermediate to the first and second longitudinally extending edges untreated, wherein the untreated portion extends along substantially the entire length of the sling, the biocompatible dissolvable protective treatment being absorbable into a patient's tissues subsequent to implantation.

2. The sling assembly of claim 1, wherein the protective treatment provides sufficient structural rigidity to the sling to inhibit the sling from longitudinally deforming during implantation.

3. The sling assembly of claim 1, wherein the protective treatment covers at least a portion of the first longitudinally extending edge of the sling along both the first and second sides.

4. The sling assembly of claim 1, wherein the protective treatment also covers at least a portion of the second longitudinally extending edge along at least one of the first and second sides.

5. The sling assembly of claim 1, wherein the protective treatment covers the first longitudinally extending edge of the sling along the first side along substantially the entire length of the sling.

6. The sling assembly of claim 1, wherein the protective treatment substantially encapsulates a portion of the first longitudinally extending edge along the first and second sides of the sling.

7. The sling assembly of claim 6, wherein the protective treatment substantially encapsulates a portion of the second longitudinally extending edge along the first and second sides of the sling.

8. The sling assembly of claim 1, wherein the sling includes first and second terminal ends and an intermediate portion located near a middle location between the first and second terminal ends and extending between the first and second longitudinally extending edges, the intermediate portion being substantially devoid of the protective treatment on at least a urethra facing side.

9. The sling assembly of claim 8, wherein the first side of the sling is the urethra facing side.

10. The sling assembly of claim 8, wherein the second side of the sling is the urethra facing side.

11. The sling assembly of claim 1, wherein the protective treatment comprises a coating.

12. The sling assembly of claim 1, wherein the protective treatment comprises an alginate.

13. The sling assembly of claim 1, wherein the protective treatment comprises a sugar based formulation.

14. The sling assembly of claim 1, wherein the protective treatment comprises a starch.

15. The sling assembly of claim 1, wherein the protective treatment comprises a gelatin.

16. The sling assembly of claim 1, wherein the protective treatment comprises cellulose.

17. The sling assembly of claim 1, wherein the protective treatment comprises polyvinyl alcohol.

18. The sling assembly of claim 1, wherein the protective treatment comprises polyglycolic acid.

19. The sling assembly of claim 1, wherein the protective treatment comprises polylactic acid.

20. The sling assembly of claim 1, wherein the protective treatment comprises polydioxinone.

21. The sling assembly of claim 1, wherein the protective treatment comprises a lubricious material.

22. The sling assembly of claim 1, wherein the protective treatment dissolves within the patient in less than about 30 minutes after the sling is implanted.

23. The sling assembly of claim 1, wherein the protective treatment dissolves within the patient in less than about 15 minutes after the sling is implanted.

24. The sling assembly of claim 1, wherein the bio protective treatment dissolves within the patient in less than about 10 minutes after the sling is implanted.

25. The sling assembly of claim 1, wherein the protective treatment dissolves within the tissues of the patient in less than about 5 minutes after the sling is implanted.

* * * * *